US012810996B2

(12) United States Patent
Westwick

(10) Patent No.: US 12,810,996 B2
(45) Date of Patent: Nov. 24, 2026

(54) SYSTEMS AND METHODS FOR COLOR FILTER ARRAY IMAGE ENHANCEMENT

(71) Applicant: Stryker Corporation, Kalamazoo, MI (US)

(72) Inventor: Paul Roald Westwick, Vancouver (CA)

(73) Assignee: Stryker Corporation, Portage, MI (US)

( * ) Notice: Subject to any disclaimer, the term of this patent is extended or adjusted under 35 U.S.C. 154(b) by 285 days.

(21) Appl. No.: 18/542,548

(22) Filed: Dec. 15, 2023

(65) Prior Publication Data

US 2024/0212832 A1 Jun. 27, 2024

Related U.S. Application Data

(60) Provisional application No. 63/477,140, filed on Dec. 23, 2022.

(51) Int. Cl.

*G06V 10/56* (2022.01)
*G06T 3/4015* (2024.01)
*G06T 5/70* (2024.01)
*G06T 5/73* (2024.01)
*G06V 10/60* (2022.01)
*G16H 30/40* (2018.01)

(52) U.S. Cl.

CPC ........... *G16H 30/40* (2018.01); *G06T 3/4015* (2013.01); *G06T 5/70* (2024.01); *G06T 5/73* (2024.01); *G06V 10/56* (2022.01); *G06V 10/60* (2022.01); *G06T 2207/10024* (2013.01); *G06T 2207/10068* (2013.01)

(58) Field of Classification Search

CPC ......... G16H 30/40; G06T 3/4015; G06T 5/70; G06T 5/73; G06T 2207/10024; G06T 2207/10068; G06V 10/56; G06V 10/60

USPC .......................................................... 382/128

See application file for complete search history.

(56) References Cited

U.S. PATENT DOCUMENTS

2009/0075391 A1* 3/2009 Fulghum, Jr. ........ A61B 5/0084 250/225
2010/0004520 A1* 1/2010 Gono .................... A61B 1/041 600/322

(Continued)

OTHER PUBLICATIONS

Geleijnse et al. (Oct. 2022). "Influence of edge enhancement applied in endoscopic systems on sharpness and noise," Journal of Biomedical Optics 27(10): 106002-1-106002-15.

(Continued)

*Primary Examiner* — Ali Bayat
(74) *Attorney, Agent, or Firm* — Morrison & Foerster LLP

(57) ABSTRACT

A method of generating an RGB image of tissue includes receiving pixel values generated by at least one color filter array imaging sensor based on light received from a scene that comprises tissue, the pixel values comprising pixel values of a plurality of different colors; converting the pixel values to a luminance-chrominance color space, wherein luminance values in the luminance-chrominance color space are generated from pixel values of only one of the plurality of different colors; performing at least one image processing procedure in the luminance-chrominance color space; and generating an RGB image of the tissue by converting from the luminance-chrominance color space to an RGB color space.

31 Claims, 7 Drawing Sheets

(56) References Cited

U.S. PATENT DOCUMENTS

| | | | | |
|---|---|---|---|---|
| 2010/0254589 | A1* | 10/2010 | Gallagher | G06V 20/695 382/133 |
| 2014/0180131 | A1* | 6/2014 | Kamimura | A61B 1/0669 600/476 |
| 2015/0182106 | A1* | 7/2015 | King | A61B 1/043 600/431 |
| 2017/0354358 | A1* | 12/2017 | Rajab | G06F 3/147 |
| 2018/0158180 | A1 | 6/2018 | Yokouchi | |
| 2020/0402207 | A1* | 12/2020 | Talbert | H04N 23/555 |
| 2022/0247979 | A1 | 8/2022 | Wada | |

OTHER PUBLICATIONS

International Preliminary Report on Patentability dated Jun. 24, 2025, directed to International Application No. PCT/US2023/084308; 11 pages.

International Search Report and Written Opinion mailed May 21, 2024, directed to International Application No. PCT/US2023/084308; 17 pages.

Messina et al. "Image Quality Improvement by Adaptive Exposure Correction Techniques," Proceedings of the 2003 International Conference on Multimedia and Expo, Jul. 6-9, 2003, Baltimore, Maryland, USA; 4 pages.

* cited by examiner

SYSTEMS AND METHODS FOR COLOR FILTER ARRAY IMAGE ENHANCEMENT

CROSS-REFERENCE TO RELATED APPLICATIONS

This application claims the benefit of U.S. Provisional Application No. 63/477,140, filed Dec. 23, 2022, the entire contents of which are hereby incorporated by reference herein.

FIELD

This disclosure generally relates to medical imaging, and more specifically, to image processing techniques for medical imaging.

BACKGROUND

Minimally invasive surgery generally involves the use of a high-definition camera coupled to an endoscope inserted through a small incision into a patient to provide a surgeon with a clear view within the body while causing minimal tissue damage. The endoscope emits light from its distal end to illuminate the surgical cavity and receives light reflected or emitted by tissue within the surgical cavity through a lens or window located at the distal end of the endoscope. The light emitted from the endoscope is generated by an illuminator that can provide a desired brightness of light to the surgical site. The light provided by the illuminator can include white light generated by combining light from different color light emitters, such as red, green, and blue light emitting diodes (LEDs).

Some medical imaging systems, such as some endoscopic imaging systems, generate color images using one or more color filter array imaging sensors. Color filter array imaging sensors couple an imaging sensor (e.g., CMOS or CCD) with a color filter array, which covers the pixels of the imaging sensor with an array of different color filters such that each pixel senses a subset of the spectrum of light received at the color filter array imaging sensor. An example of a color filter array is a Bayer filter array, which includes a particular arrangement of red, green, and blue filters. The patchwork of color information in the raw image data from a color filter array image sensor is converted to full-color image using a demosaicing technique. Demosaicing can include spatially interpolating the color value of the pixels of the same color in the neighborhood to produce each color value for each pixel.

The filters in color filter arrays do not perfectly filter light of spectral bands outside of the desired spectral band. For example, a green filter may pass some amount of red and blue light as well as green, though to a lesser extent. Thus, the signal from a given color pixel may reflect some contribution of light of other colors. Such "leakage" can be accounted for when generating a full-color image from the raw sensor data by applying leakage correction to the data from the imaging sensor.

Some image processing is performed on the luminance channel of an image. Known techniques are used to convert from RGB color space to luminance-chrominance color space. This color space conversion when applied to pixel values from a color filter array imaging sensor is typically performed on leakage corrected pixel values.

SUMMARY

According to an aspect, systems and methods for generating color images using a color filter array image sensor include converting the pixel values to a luminance-chrominance color space using the pixel values associated with only one of the colors of the color filter array image sensor to generate the luminance values for the luminance-chrominance color space. One or more image processing steps, such as sharpening, can then be performed on the luminance values. A full-color image is then generated by converting from the luminance-chrominance color space to RGB color space. Generating the luminance values directly from the pixel values associated with only one of the colors of the color filter array image sensor avoids introducing noise amplification associated with leakage correction into the image processing performed on the luminance channel, which improves the resulting RGB image.

According to an aspect, a method of generating an RGB image of tissue includes receiving pixel values generated by at least one color filter array imaging sensor based on light received from a scene that comprises tissue, the pixel values comprising pixel values of a plurality of different colors; converting the pixel values to a luminance-chrominance color space, wherein luminance values in the luminance-chrominance color space are generated from pixel values of only one of the plurality of different colors; performing at least one image processing procedure in the luminance-chrominance color space; and generating an RGB image of the tissue by converting from the luminance-chrominance color space to an RGB color space.

The pixel values may include red, green, and blue pixel values. The luminance values may be generated from only the green pixel values.

At least some of the luminance values may be equal to corresponding pixel values of the only one of the plurality of different colors. At least some of the luminance values may be generated by spatially interpolating based on pixel values of the only one of the plurality of different colors.

The light received from the scene may include reflected light generated by different color illuminators of an illumination system. The chrominance values of the chrominance-luminance color space image may be calculated from weights determined based on a response of the at least one color filter array imaging sensor to light generated by the different color illuminators of the illumination system. The at least one color filter array imaging sensor may include red, green, and blue pixels and the different color illuminators comprise red, green, and blue illuminators.

Weights used for converting the pixel values to the luminance-chrominance color space may be used to convert from the luminance-chrominance color space to the RGB color space for generating the RGB image of the tissue.

The scene may be an endoscopic scene.

The at least one image processing procedure may include at least one of sharpening, denoising, feature extraction, and image stabilization.

Converting the pixel values to a luminance-chrominance color space may include demosaicing and leakage correction.

The at least one color filter array imaging sensor may include a Bayer sensor.

According to an aspect, a system includes one or more processors, memory, and one or more programs stored in the memory for execution by the one or more processors and including instructions for: receiving pixel values generated by at least one color filter array imaging sensor based on light received from a scene that comprises tissue, the pixel values comprising pixel values of a plurality of different colors; converting the pixel values to a luminance-chrominance color space, wherein luminance values in the luminance-chrominance color space are generated from pixel values of only one of the plurality of different colors; performing at least one image processing procedure in the luminance-chrominance color space; and generating an RGB image of the tissue by converting from the luminance-chrominance color space to an RGB color space.

The system may include an imager that may include the at least one color filter array imaging sensor. The imager may include an endoscopic imager. The endoscopic imager may be a chip-on-tip endoscope.

The system may include an illumination system for illuminating the scene.

The pixel values may include red, green, and blue pixel values. The luminance values may be generated from only the green pixel values.

At least some of the luminance values may be equal to corresponding pixel values of the only one of the plurality of different colors. At least some of the luminance values may be generated by spatially interpolating based on pixel values of the only one of the plurality of different colors.

The light received from the scene may include reflected light generated by different color illuminators of an illumination system. The chrominance values of the chrominance-luminance color space image may be calculated from weights determined based on a response of the at least one color filter array imaging sensor to light generated by the different color illuminators of the illumination system. The at least one color filter array imaging sensor may include red, green, and blue pixels and the different color illuminators comprise red, green, and blue illuminators.

Weights used for converting the pixel values to the luminance-chrominance color space may be used to convert from the luminance-chrominance color space to the RGB color space for generating the RGB image of the tissue.

The scene may be an endoscopic scene.

The at least one image processing procedure may include at least one of sharpening, denoising, feature extraction, and image stabilization.

Converting the pixel values to a luminance-chrominance color space may include demosaicing and leakage correction.

The at least one color filter array imaging sensor may include a Bayer sensor.

A non-transitory computer readable storage medium storing one or more programs for execution by one or more processors of a computing system, the one or more programs comprising instructions that when executed by the one or more processors cause the computing system to perform any of the above methods.

A computer program product comprises one or more software code portions for execution by one or more processors of a computing system, the one or more software code portions comprising instructions that when executed by the one or more processors cause the computing system to perform any of the above methods.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE FIGURES

The invention will now be described, by way of example only, with reference to the accompanying drawings, in which.

DETAILED DESCRIPTION

Figure 1:
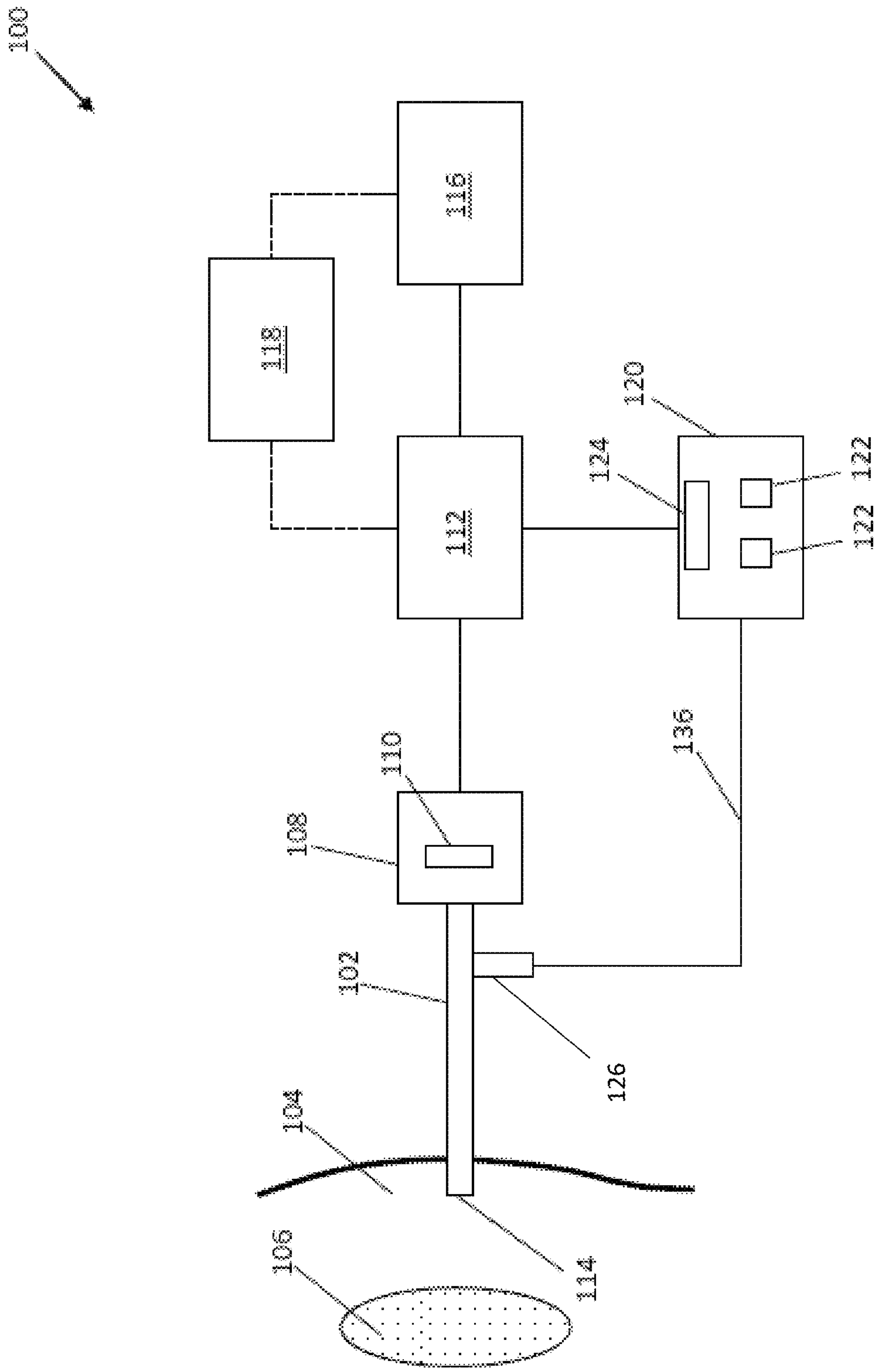
FIG. 1 illustrates an exemplary system for endoscopic imaging.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein are systems and methods for enhancing medical images captured using a color filter array image sensor. A color image can be converted from a given color space, such as red, green, blue color space, to a luminance-chrominance color space, one or more enhancements can be performed on the luminance channel, and an enhanced image can be generated by converting back to the given color space. When converting to the luminance-chrominance color space, the luminance channel is generated using pixel values corresponding to only one of the colors of the color filter array image sensor. Generating the luminance values from the pixel values associated with only one of the colors of the color filter array image sensor avoids introducing noise amplification associated with leakage correction into the enhancement performed on the luminance channel, which improves the resulting color image relative to conventional color space conversion techniques.

Medical imaging frequently includes image processing for improving image quality. Examples of image processing include sharpening and smoothing. Human vision is more sensitive to spatial differences in luminance than in color. So, many image enhancement techniques are applied to the luminance channel of an image.

Conventionally, the luminance channel of an image is calculated from a weighted sum of the color pixel values of the image, where the weights correspond with the relative contribution to brightness by each color. Weights are defined according to different standards. For example, the standard specified by the International Telecommunications Union Radiocommunication Sector (ITU-R) in Recommendation BT.709 (Rec. 709) defines luminance as:

$$L = 0.2126 * \text{Red} + 0.7152 * \text{Green} + 0.0722 * \text{Blue}$$

Thus, green provides the biggest contribution to luminance. This reflects the higher sensitivity of the human eye to light in the green waveband than in the blue and red wavebands.

Color filter arrays are designed to pass a single color for each pixel. For example, a Bayer filter array includes red, green, and blue filters, one for each pixel. However, a color filter array does not filter perfectly, and each filter will pass some amount of light from other colors. In other words, using a Bayer sensor as an example, when the Bayer sensor is exposed to light having a combination of red, green, and blue light, a green pixel (a pixel covered by a green filter) may detect some amount of blue and red light in addition to the green light. Thus, the signal from a green pixel from light reflected from a scene that includes green, blue, and red light is a weighted sum of the green, blue, and red light. Conventionally, leakage correction is applied to the pixel values of a color filter array sensor to determine the "actual" amount of a given color of light at a given pixel. In other words, using a green pixel of a Bayer sensor as an example, leakage correction seeks to extract only the contribution of green light to the signal generated by a green pixel, subtracting out the contribution of blue and red light. Leakage correction generally includes applying a weighted sum of the pixel values for the different colors. The weights are based on the response of the particular Bayer sensor to light of a given spectral distribution and can be experimentally determined. Leakage correction typically includes enhancing the color of interest and subtracting out some portion of the other colors. So, for example, to get the blue value, the raw blue signal is amplified and some portion of the red and green signals are subtracted. Because of the amplification, leakage correction often amplifies noise.

According to various aspects, an imaging system may include a color filter array image sensor in which green pixel values are weighted sums of the contribution of red, green, and blue light in similar proportions to the contributions of red, green, and blue pixel values to the luminance channel of an image. Taking advantage of this similarity, uncorrected green pixel values can be used as luminance values, which avoids the need to calculate luminance values from leakage corrected red, green, and blue values. In other words, instead of the conventional technique of applying leakage correction to raw red, green, and blue pixel values to calculate estimates of actual red, green, and blue light received at the color filter array image sensor, and then calculating the luminance from the leakage corrected red, green, and blue pixel values, systems and methods described herein can use the uncorrected green pixel values as the luminance values because the uncorrected green pixel values have contributions from red, green, and blue light in similar proportions to the contributions of red, green, and blue light to luminance. This not only eliminates the need to calculate luminance, it has the added benefit of avoiding the noise amplification that can result from leakage correction. One or more image processing enhancements can then be applied to the luminance values, meaning that noise amplification arising from leakage correction is not introduced into the image enhancement steps. Once the image enhancement performed on the luminance values is complete, an RGB image can be generated by converting from luminance-chrominance color space to RGB color space.

As noted above, converting from the raw pixel values to luminance-chrominance color space includes using the green pixel values as the luminance values of the luminance-chrominance color space. The chrominance values can be calculated based on leakage corrected red, green, and blue pixel values. Leakage corrected red, green, and blue pixel values can be calculated using leakage correction weights that are determined experimentally for the color filter array sensor and illumination system. For example, the color filter array sensor can be exposed to light from the illumination system, which has a known spectral distribution, and the response of the color filter array sensor can be compared to the known spectral distribution to determine leakage correction weights that can be used to correct the red, green, and blue pixel values to match the known spectral distribution.

The leakage correction weights determined for a color filter array sensor and illumination source can be used to calculate leakage corrected red, green, and blue pixel values from the pixel data generated by the same color filter array sensor based on light received from the same illumination source. The following equation explains the relationship between the sensor pixel values and the actual red, green, and blue light received by the sensor.

$$\begin{bmatrix} Rsens \\ Gsens \\ Bsens \end{bmatrix} = \begin{bmatrix} Rr & Rg & Rb \\ Gr & Gg & Gb \\ Br & Bg & Bb \end{bmatrix} \begin{bmatrix} R' \\ G' \\ B' \end{bmatrix} \quad \text{(Equation 1)}$$

Where Rsens, Gsens, and Bsens are the red, green, and blue pixel values generated by the color filter array sensor and R', G', and B' are the actual magnitudes of red, green, and blue light received at the sensor. The 3×3 matrix includes the leakage correction weights that define the relative amount of the given color of light that is sensed by a given color pixel. So, for example, the green pixel senses a combination of red, green, and blue light according to the following equation:

$$Gsens = GrR' + GgG' + GbB'$$

Where Gr, Gg, and Gb are the leakage correction weights that characterize how much the respective colors incident on the green pixels contribution to the magnitude of light sensed by the green pixels. Exemplary values for these weights are Gr=0.27, Gg=0.61, and Gb=0.12.

The leakage correction weights are constants for the color filter array sensor and illumination system. Using equation 1, the actual magnitudes of red, green, and blue light received at the sensor (the leakage corrected red, green, and blue pixel values) from light generated by the illumination system and reflected by the scene can be determined by multiplying the sensor pixel values by the inverse of the leakage correction weight matrix to solve for R', G', and B'.

From the leakage corrected red, green, and blue values (R', G', and B' in equation 1 above), color space conversion can be conducted to convert from the RGB color space to luminance-chrominance color space. This conversion can be done using known color space conversion algorithms, such as the following color space conversion algorithm:

$$\begin{bmatrix} Y \\ Cb \\ Cr \end{bmatrix} = \begin{bmatrix} K_R & K_G & K_B \\ -\frac{1}{2}\cdot\frac{K_R}{1-K_B} & -\frac{1}{2}\cdot\frac{K_G}{1-K_B} & \frac{1}{2} \\ \frac{1}{2} & -\frac{1}{2}\cdot\frac{K_G}{1-K_R} & -\frac{1}{2}\cdot\frac{K_B}{1-K_R} \end{bmatrix} \begin{bmatrix} R' \\ G' \\ B' \end{bmatrix} \quad \text{(Equation 2)}$$

Y is the luminance channel and Cb and Cr are the blue-difference and red-difference chrominance channels. R', G', and B' are the leakage corrected red, green, and blue pixel values. $K_R$, $K_G$, and $K_B$ are the weights that define the proportional contribution of the red, green, and blue light to the luminance channel.

Existing digital imaging standards define values for weights for converting from RGB color space to luminance-chrominance color space. For example, the International Telecommunications Union Radiocommunication Sector (ITU-R) Recommendation BT.709 (Rec. 709) specifies these weights (also referred to as "priors") as: $K_R$=0.2126, $K_G$=0.7152, and $K_B$=0.0722, and ITU-R Recommendation BT.2020-2 (Rec. 2020-2) specifies the weights as $K_R$=0.2627, $K_G$=0.6780, and $K_B$=0.0593.

Comparing the weights defined by Rec. 709 and Rec. 2020-2 to the exemplary weights for the contribution of red, green, and blue light to the green sensor signal provided above (Gr=0.27, Gg=0.61, and Gb=0.12), it can be seen that the relative contribution of red, green, and blue light to the green pixel signal is similar to the relative contribution of red, green, and blue light to the luminance defined by Rec. 709. Since the green pixel values have similar proportional contributions of red, green, and blue light as the luminance channel, the green pixel values can be good estimates of the luminance. As such, according to the principles described here, the green pixel values can be used as the luminance channel values, which avoids having to calculate luminance from leakage corrected red, green, and blue values. This avoids introducing leakage correction noise amplification to the luminance channel and, thereby, avoids introducing noise amplification into image enhancement steps performed on the luminance channel.

The chrominance values for the luminance-chrominance color space are calculated using Equation 2, where $K_R$, $K_G$, and $K_B$ are set to Gr, Gg, and Gb, respectively, and the leakage corrected red, green, and blue pixel values are used for R', G', and B'. After any image enhancement techniques are applied to the luminance channel and/or the chrominance channels, color space conversion is used to generate RGB channels from the luminance and chrominance values using equation 2 and solving for R', G', and B'.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general-purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates an exemplary system 100 for endoscopic imaging. System 100 includes an endoscope 102 for insertion into a surgical cavity 104 for imaging tissue 106 within the surgical cavity 104 during a medical procedure and an illuminator 120 that provides illumination light to the endoscope 102, which emits the light from its distal end 114 for illuminating the tissue 106.

The endoscope 102 may extend from an endoscopic camera head 108 that includes one or more imaging sensors 110. As is well known in the art, light reflected and/or emitted (such as fluorescence light emitted by fluorescing targets that are excited by fluorescence excitation illumination light) from the tissue 106 is received by the distal end 114 of the endoscope 102. The light is propagated by the endoscope 102, such as via one or more optical components (for example, one or more lenses, prisms, light pipes, or other optical components), to the camera head 108, where it is directed onto the one or more imaging sensors 110. According to various embodiments, one or more filters (not shown) may be included in the endoscope 102 and/or camera head 108 for filtering a portion of the light received from the tissue 106 (such as fluorescence excitation light).

The one or more imaging sensors 110 detect light received from the imaging field of view, including tissue 106. The one or more imaging sensors 110 may be configured to output digital pixel data. The digital pixel data may be transmitted to the camera control unit 112, which can process the digital pixel data to generate one or more images. As used herein "images" and "imaging data" encompasses single images and video frames. The images can be transmitted to an image processing unit 116 for further image processing, storage, display, and/or routing to an external device (not shown).

The images can be transmitted to one or more displays 118, from the camera control unit 112 and/or the image processing unit 116, for visualization by medical personnel, such as by a surgeon for visualizing the field of view within the surgical cavity 104 during a surgical procedure on a patient. Optionally, one or more functions of the image processing unit 116 described herein can be performed by the camera control unit 112 and vice versa.

The illuminator 120 generates illumination light and provides the illumination light to the endoscope 102 via light guide 136, which may comprise, for example, one or more fiber optic cables, with the light guide 136 coupled to the endoscope 102 at the light post 126 in the proximal region of the endoscope. The illumination light is emitted from the distal end 114 of the endoscope 102 and illuminates the tissue 106. As used herein, "illumination light" refers to light that may be used to illuminate tissue for the purposes of imaging the tissue. The illumination light can include any desirable wavebands or combination of wavebands. At least a portion of the illumination light may be light having a waveband in the visible spectrum that is reflected by the tissue 106 and captured by the one or more imaging sensors 110 for generating reflected light imaging data. Optionally, the illumination light can be or include fluorescence excitation light for exciting one or more fluorescing targets in the tissue, which can include one or more fluorescence agents and/or one or more auto-fluorescing targets. Light emitted by the one or more fluorescence targets may be captured by the one or more imaging sensors for generating fluorescence imaging data. Optionally, visible light and fluorescence excitation light can be provided based on an operating mode, such as a visible light imaging operating mode in which the illuminator provides only visible light, a fluorescence imaging mode in which the illuminator provides only fluorescence excitation light, and/or a combined imaging mode in which both visible light and fluorescence excitation light are provided, either simultaneously or in alternating fashion.

The illuminator 120 includes one or more light sources 122 that each generate one or more wavebands of light and a controller 124 for controlling the light sources 122. The light sources 122 generate illumination light for illuminating the tissue 106 via the endoscope 102. The controller 124 can be configured to activate and deactivate the individual light sources 122 and/or adjust a power level of the light sources 122 to adjust the level of intensity (i.e., the luminance) of light generated by the individual light sources 122. The controller 124 may control one or more light sources 122 based on one or more control signals received from camera control unit 112 and/or image processing unit 116. In some embodiments, control signals received from the camera control unit 112 and/or image processing unit 116 can instruct the controller 124 how to control individual light sources 122, such as by including instructions to activate or deactivate individual light sources 122 and/or to set one or more individual light sources 122 at a specified power/intensity level. For example, the camera control unit 112 and/or image processing unit 116 may determine that a specific color and/or intensity adjustment is needed based on analysis of pixel data generated by the endoscopic camera head 108 and the controller 124 may receive instructions specifying the adjustments.

Figure 2:
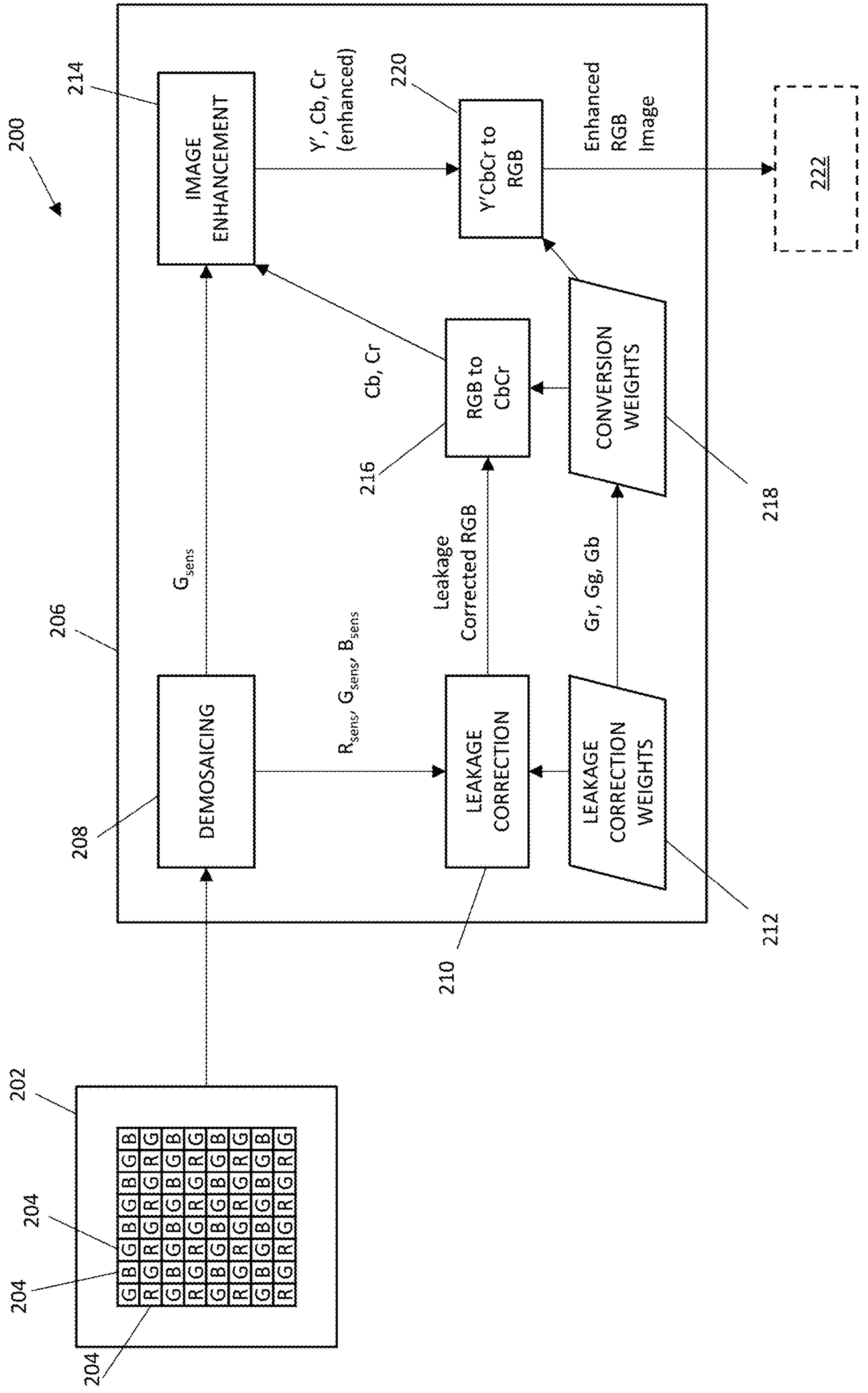
FIG. 2 is a functional block diagram of portions of an exemplary imaging system that performs luminance-based image enhancement using pixel values of one of a plurality of colors detected by a color filter array sensor.

FIG. 2 is a functional block diagram of portions of an exemplary imaging system 200 that performs luminance-based image enhancement using pixel values of one of a plurality of colors detected by a color filter array sensor, according to the principles described herein. System 200 can perform luminance-based image enhancement without introducing noise into the luminance channel from the color correction that is typically required for color filter array sensors. System 200 can be used for system 100 of FIG. 1. The blocks of system 200 described below are intended to convey the functions performed by system 200 and are not intended to imply that various functions are necessarily performed by discrete components. For example, all functions performed by the blocks of system 200 may be performed by one or more processors programmed and/or otherwise configured to perform the various functions. Additionally, one or more functions may be combined into a single processing step or may be performed in multiple processing steps. For example, demosaicing and leakage correction can be performed in the same processing step or different processing steps.

System 200 includes at least one color filter array sensor 202, which can be used for the one or more imaging sensors 110 of FIG. 1. As is well-known in the art, the color filter array sensor 202 includes an array of different waveband filters positioned in front of light sensing pixels 204 so that the sensor 202 can separately sense different colors of light received from a scene. For example, the color filter array sensor 202 can be a Bayer sensor, which as is well-known in the art, includes a 2×2 pattern of one red filter ("R"), two green filters ("G"), and one blue filter ("B"). The color filter array sensor 202 is not limited to a Bayer filter array and can include other filter arrays, including arrays having a different pattern of red, green, and blue filters, arrays having red, green, blue, and infrared filters, arrays having red, green, blue, and white filters, and arrays having cyan, yellow, and magenta filters, with or without infrared filters.

Figure 3:
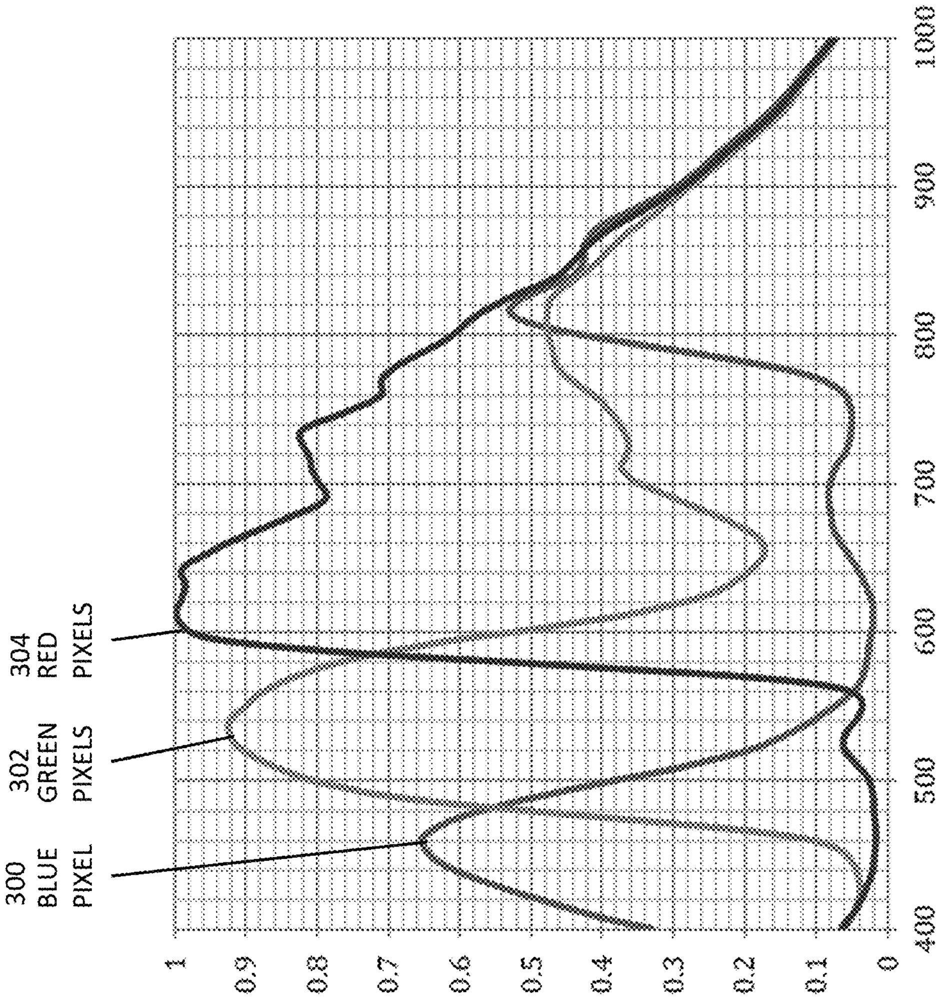
FIG. 3 is a set of exemplary response curves for a color filter array sensor exposed to broadband light, which illustrates leakage.

The color filter array sensor 202 outputs digital pixel data. With respect to the example of the color filter array sensor 202 illustrated in FIG. 2, the sensor outputs either a red pixel value, a green pixel value, or a blue pixel value for each pixel 204. As is known in the art, color filter arrays do not perfectly filter light, meaning that pixels respond to at least some light that is outside of the desired light band of the corresponding filter. This is often referred to as leakage. FIG. 3 is a set of exemplary response curves for a color filter array sensor exposed to broadband light, which illustrates leakage. The response curve 300 for blue pixels shows that blue pixels have some response to red light (centered at 650 nm) and significant response to infrared light (generally above 700 nm). The response curve 302 for green pixels shows that green pixels have some response to blue light (centered at 450 nm) and some response to red and infrared light. The response curve 304 for red pixels shows some response to green light. Therefore, due to leakage, the pixel data output by the sensor 202 is typically not entirely accurate in terms of the amount of the corresponding color of light received at each pixel. As described above and detailed further below, this trait can be utilized for generating a luminance channel for image enhancement without requiring a leakage correction step that would amplify noise in the enhancement.

System 200 includes one or more processors 206 (often hereinafter referred to as processor 206 for simplicity) for processing the pixel data received from the color filter array sensor 202. With reference to system 100 of FIG. 1, the one or more processors 206 can include one or more processors of the camera head 108, one or more processors of the camera control unit 112, and/or one or more processors of image processing unit 116. The one or more processors 206 are configured (e.g., programmed) to implement the functional blocks illustrated in FIG. 2 and discussed further below.

Demosaicing block 208 includes demosaicing the digital image data from the color filter array sensor 202. As is known in the art, demosaicing includes generating each of the colors represented in the digital image data for each pixel location. For example, with respect to the color filter array sensor configuration of FIG. 2, demosaicing generates red, green, and, blue pixel values for each pixel location of the sensor. Demosaicing generally includes interpolating pixel values from one or more nearby pixel values. The results of the demosaicing operation are values for each color of the color filter array sensor 202 ("Rsens", "Gsens", "Bsens" in FIG. 2) for each pixel 204.

Leakage correction block 210 corrects for the leakage affecting the pixel data generated by color filter array sensor 202. Leakage correction includes calculating a weighted sum of the red, green, and blue pixel data to generate corrected red, green, and blue pixel values, such as according to the relationship of equation (1) above. A set of leakage correction weights 212 (also referred to as "priors") are used to calculate the weighted sum. The leakage correction weights 212 are predetermined based on the response of the color filter array sensor 202 to light used for illuminating a scene, such as light generated by illuminator 120 of system 100. The output of leakage correction block 210 is a set of leakage corrected red, green, and blue pixel values for each pixel 204.

Image enhancement block 214 applies one or more image enhancement algorithms in luminance-chrominance color space, including one or more image enhancement algorithms applied to the luminance channel (e.g., sharpening). As known in the art, the luminance channel includes a weighted sum of different colors, such as a weighted sum of red, green, and blue light. For example, ITU-R Rec. 709 specifies luminance of a given pixel as 21.26% of the red light at the pixel, 71.52% green light at the pixel, and 7.22% blue light at the pixel. As explained above, the signal generated by pixels of color filter array sensors may include contributions from multiple wavebands in addition to the waveband of the filter associated with the pixel. Depending on the color filter array sensor and the illumination provided to the scene, pixels of a particular color may detect different colors in similar proportion to the contributions of the colors to the luminance channel. For example, with reference to FIG. 3, the light sensed by a green pixel (response curve 302) may be about 27% red light, 61% green light, and 12% blue light. Taking advantage of the similarity between the different color contributions to the light sensed by a particular color pixel and the different color contributions to luminance, the light sensed by the particular color pixel is used as the luminance by the image enhancement block 214. For example, the demosaiced green pixel data ($G_{sens}$) may be used as the luminance channel by image enhancement block 214. Because leakage correction can amplify noise, using the uncorrected green pixel values for the luminance channel avoids introducing leakage-correction based noise to the luminance channel, resulting in lower noise in the enhanced RGB image output by system 200.

Image enhancement block 214 may additionally apply one or more image enhancement algorithms to one or both chrominance channels. The chrominance channels are calculated by an RGB to chrominance converting block 216 using equation (2) above, the leakage corrected RGB values from the leakage correction block 210, and a set of conversion weights 218. As shown in equation (2) above, the set of conversion weights for calculating the luminance and chrominance from red, green, and blue values can be represented as functions of the relative contributions of red, green, and blue light to luminance, which are denoted $K_R$, $K_G$, and $K_B$ in equation (2). Since the luminance channel is set to the uncorrected green pixel values, the conversion weights 218 used by the RGB to chrominance converting block 216 for calculating the chrominance channels are based on the leakage correction weights for the green pixel values ($G_r$, $G_g$, and $G_b$). Referring to equation (2) above, setting the weights ($K_R$, $K_G$, and $K_B$) for calculating luminance from leakage corrected red, green, and blue values to the green leakage correction weights ($G_r$, $G_g$, and $G_b$) results in the calculated luminance being equal to the uncorrected green pixel values (Gsens) used by the image enhancement block 214, which means that calculating the chrominance channels based on these same green leakage correction weights ($G_r$, $G_g$, and $G_b$) results in the calculated chrominance channels being consistent with the luminance channel. Thus, the RGB to chrominance converting block 216 calculates the chrominance channels using equation (2) and a set of conversion weights 218 that are based on setting $K_R$, $K_G$, and $K_B$ equal to the respective green leakage correction weights ($G_r$, $G_g$, and $G_b$).

The image enhancement block 214 outputs enhanced pixel values in luminance-chrominance color space based on the one or more image enhancement techniques that it implements. Color space conversion block 220 converts from this luminance-chrominance color space to RGB color space using the same conversion weights 218 used by the RGB to chrominance converting block 216 (reversing equation (2)). Color space conversion block 220 outputs the resulting enhanced RGB image, which can be provided to one or more downstream subsystems or systems 222, such as a display, an image processing system, a storage unit, etc. For example, with respect to FIG. 1, the enhanced RGB image could be provided from camera control unit 112 to one or more displays 118 and/or image processing unit 116 for further image processing.

Figure 4:
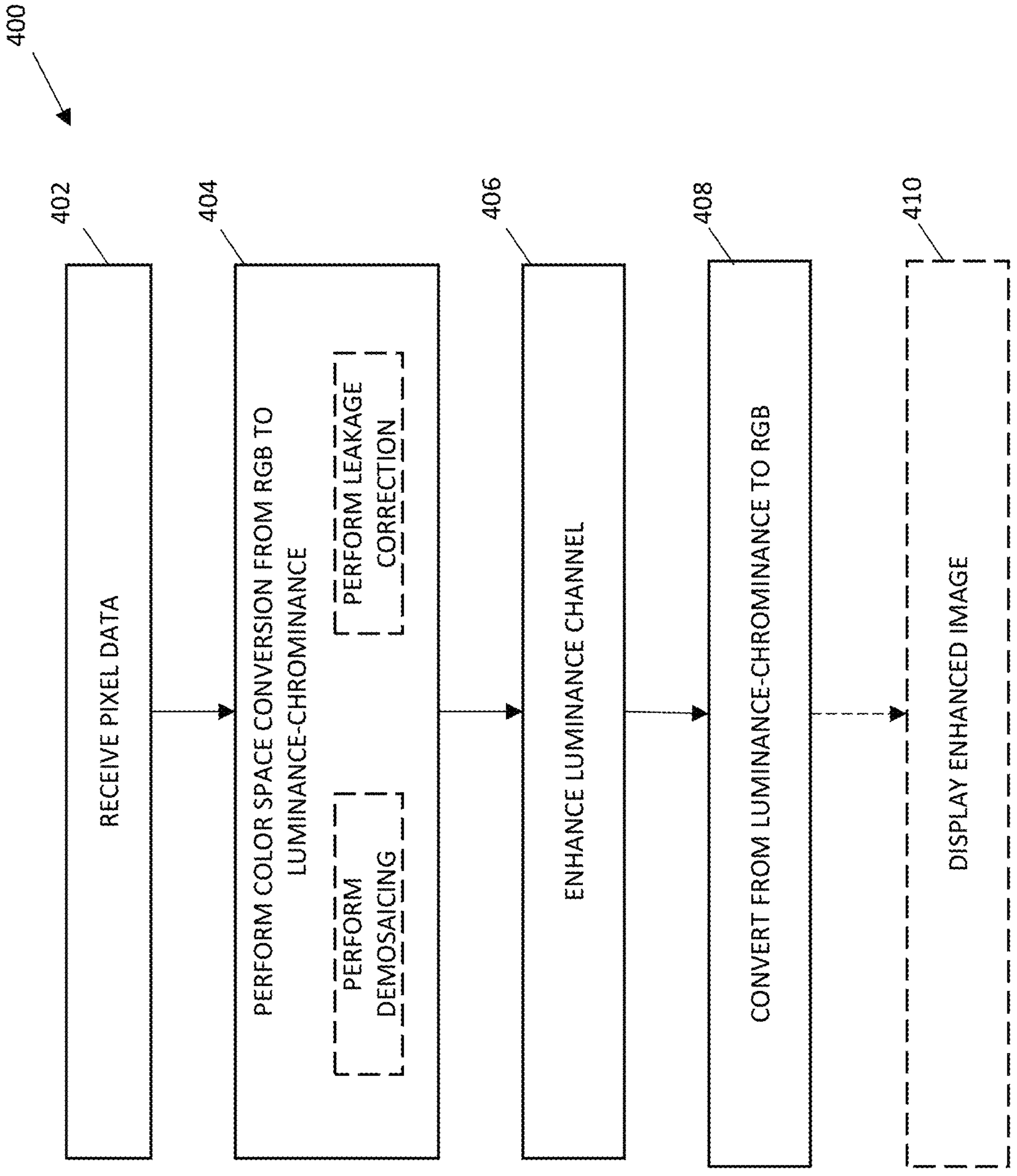
FIG. 4 is a diagram of an exemplary method for generating an enhanced RGB image based on performing luminance-based image enhancement using pixel values of one of a plurality of colors detected by a color filter array sensor.

FIG. 4 is an exemplary diagram of a method 400 for generating an enhanced RGB image based on performing luminance-based image enhancement using pixel values of one of a plurality of colors detected by a color filter array sensor. Method 400 can be performed by one or more processors configured and/or programmed to perform the steps of method 400. Method 400 can be performed by an imager that comprises the color filter array sensor or can be performed by a system that receives pixel data from an imager. Referring to FIG. 1, one or more steps of method 400 can be performed by camera head 108 of system 100 and/or by camera control unit 112. The endoscope 102 can be inserted into the surgical cavity 104 prior to start of the method 400.

At step 402, pixel values are received from at least one color filter array imaging sensor. For example, with reference to system 200 of FIG. 2, one or more processors 206 receive pixel values from one or more color filter array sensors 202. The at least one color filter array imaging sensor senses light from a scene that is illuminated by an illumination system, such as illuminator 120 of FIG. 1. The imaged scene may include tissue within a surgical cavity that is being illuminated by the illumination system. The pixel values may have been captured prior to the start of the method 200. Generally, the pixel values are digital values corresponding to the intensity of light received by the pixels of the one or more color filter array sensors 202 from the scene. The received light can include light reflected from the tissue and/or light generated by one or more fluorescing components in the tissue. The pixel values include pixel values for each color of the plurality of colors of the color filter array sensor. For example, the color filter array sensor may be a Bayer sensor and the pixel values can include, for each pixel location, either a red pixel value, a green pixel value, or a blue pixel value depending on the color filter associated with the pixel location.

At step 404, the pixel values are converted from the color space associated with the color filter array to luminance-chrominance color space. For example, for a color filter array that has red, green, and blue pixels, the pixel values are converted from red, green, and blue color space to luminance-chrominance color space. This step can optionally include demosaicing to generate a value for each color for each pixel. Any suitable demosaicing algorithm for the color filter array can be used. For example, a value for a given color at a particular pixel location not associated with that color (e.g., a green value for a red pixel) can be interpolated from values for the given color from nearby (e.g., directly adjacent) pixel locations. Alternatively, demosaicing can be performed before or after color conversion in step 404.

The luminance values in the color space conversion of step 404 are generated from pixel values of only one of the plurality of colors of the color filter array sensor. For example, for a Bayer sensor, the luminance values can be generated from only the green pixels. Specifically, the demosaiced green pixel values can be used as the luminance values.

The particular color pixel values that are used for generating the luminance values can be selected based on a similarity between the proportion of the different colors of light that are detected by the particular color pixel and the contribution of the different colors of light to the conventional calculation of luminance. As explained above, filters in a color filter array do not perfectly filter light, resulting in a given pixel sensing light in wavebands outside of the color of the filter associated with the given pixel. For example, a green pixel may sense light outside of the green waveband. The imaging system, including the one or more color filter array imaging sensors and the illumination system, may be configured such that the relative contribution of different colors reflected by a scene (based on illumination provided by the illumination system) to a particular color pixel of the one or more color filter array sensors is proportional to the relative contribution of those colors to a conventional calculation of luminance from those colors. As such, the pixel values for the particular color may be used (e.g., after demosaicing) as the luminance channel in the conversion from the color space associated with the color filter array to luminance-chrominance color space. For example, the demosaiced green pixel values of a Bayer sensor may be used as the luminance values.

As explained above, using the pixel values for a given color as the luminance values avoids the necessity to use leakage corrected pixel values for generating the luminance channel. Since leakage correction can amplify noise, avoiding leakage correction in generating the luminance channel avoids introducing the noise amplification into the luminance channel and, thereby, into an image enhancements applied to the luminance channel, thus providing improved image enhancement.

Color space conversion in step 404 can also include generating the chrominance channels for the luminance-chrominance color space. This can be done by converting leakage corrected values of the color space of the color filter array sensor to luminance-chrominance values. For example, for a Bayer sensor, leakage corrected red, green, and blue values can be generated for demosaiced pixel values and these values can be converted to luminance-chrominance values. Demosaicing and generating leakage corrected values can be done in the same calculation or in different calculations.

Figure 5A:
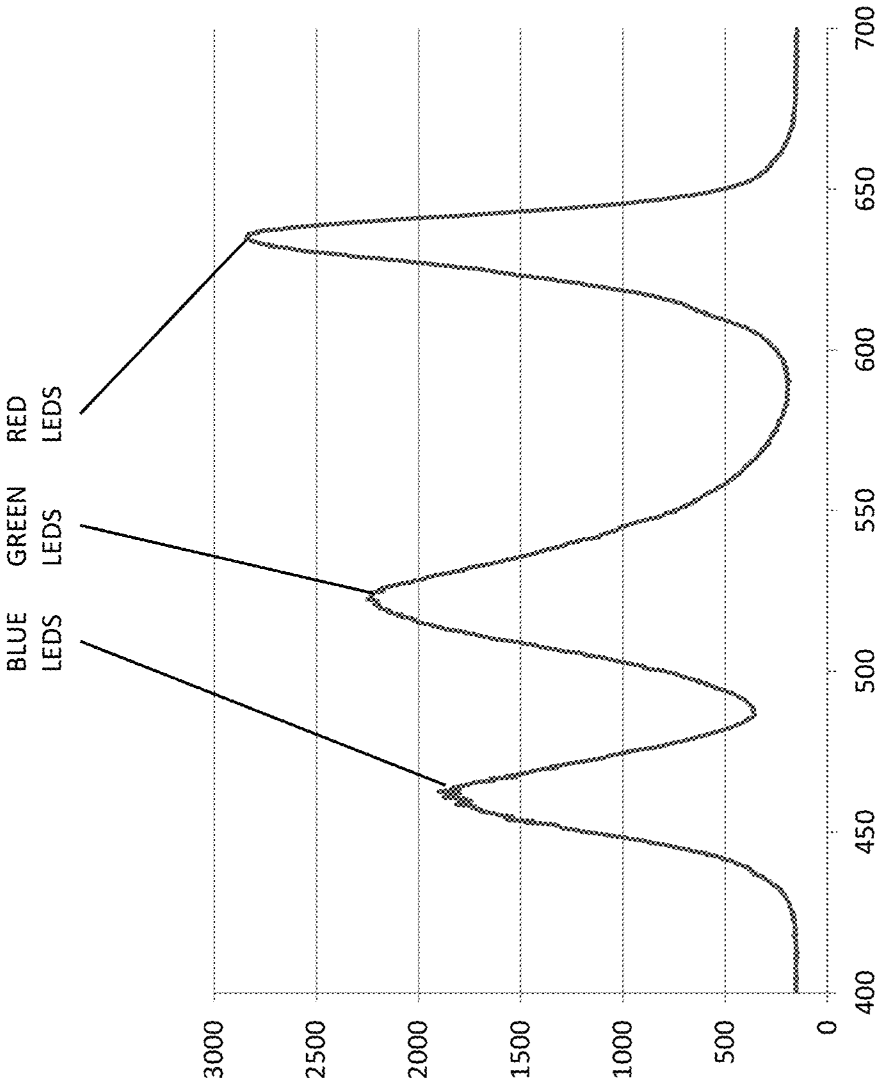
FIG. 5A illustrates an example of the spectrum provided by an exemplary illuminator that includes red, green, and blue light generators.
Figure 5B:
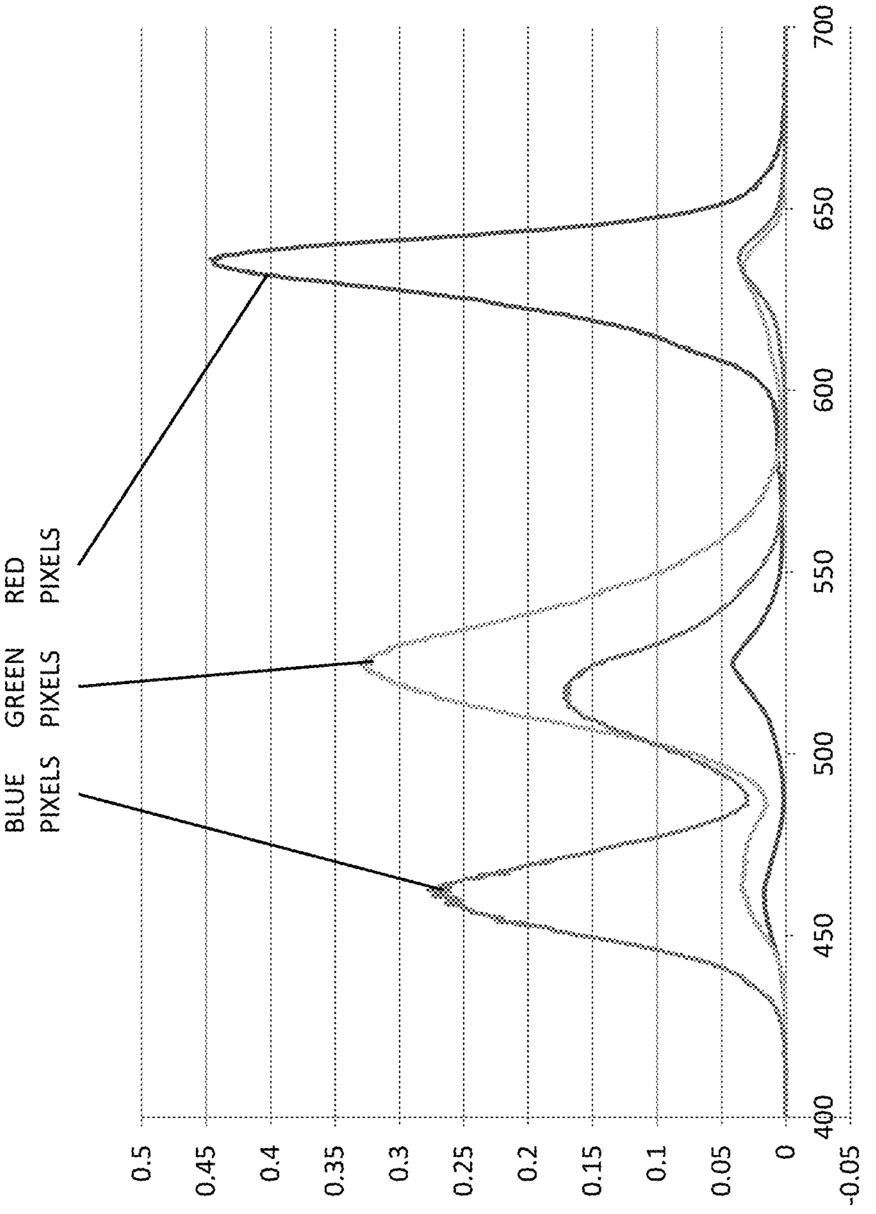
FIG. 5B illustrates an example of the response of red, green, and blue pixels of an exemplary color filter array sensor to the spectrum of FIG. 5A.

Leakage correction of the pixel values from the color filter array sensor for generating the chrominance channels can be done using leakage correction weights (e.g., leakage correction weights 212 of FIG. 2). The leakage correction weights are predetermined based on testing the response of the imaging sensor (e.g., imaging sensor 110 of FIG. 1) to light provided by the illuminator of the imaging system (e.g., illuminator 120 of FIG. 1). FIG. 5A illustrates an example of the spectrum provided by an exemplary illuminator (e.g., illuminator 120 of FIG. 1) that includes red, green, and blue light generators (e.g., LEDs). FIG. 5B illustrates an example of the response of red, green, and blue pixels of an exemplary color filter array sensor (e.g., imaging sensor 110 of FIG. 1) to the spectrum of FIG. 5A. As illustrated, each exemplary color pixel responds to light of each color to different degrees. To characterize and correct for this leakage, the color filter array sensor can be exposed to one of the colors from the illuminator at a time and the response for each color pixel can be used to calculate the relative proportion of each illumination color to the response of each color pixel. The leakage correction weights include weights for the illumination colors for each color pixel. For a red, green, blue color space, the leakage correction weights are represented in equation (1) above by the 3×3 matrix. With reference to equation (1), leakage corrected red, green, and blue values are calculating by multiplying the inverse of the 3×3 matrix by the red, green, and blue pixel values from the sensor (which may be demosaiced or are demosaiced in the same calculation).

The leakage corrected color values are then converted to chrominance values using a conversion algorithm, such as equation (2) above, and a set of weights (e.g., weights 218 of FIG. 2). So that the chrominance values are consistent with the luminance values, the leakage correction weights for the color used for the luminance channel (e.g., the green leakage correction weights, $G_r$, $G_g$, $G_b$ in FIG. 2) are used for generating the weights for the chrominance conversion. For example, with reference to the RGB to luminance-chrominance conversion of equation (2) and assuming that the non-leakage corrected green pixel values are used for the luminance channel, the leakage correction weights for green pixels are used for weights $K_R$, $K_G$, and $K_B$.

At step 406, one or more enhancement techniques are applied to the luminance channel. For example, one or more algorithms for sharpening, denoising, feature extraction, and/or image stabilization can be applied to the luminance channel. One or more enhancement techniques may also be applied to one or more of the chrominance channels. For example, a smoothing algorithm can be applied to the chrominance channels.

At step 408, an enhanced RGB image can be generated by converting from the luminance-chrominance color space to RGB color space. This is done by multiplying the luminance and chrominance channels by the inverse of the weight matrix of equation (2), using the same weights used for generating the chrominance values (e.g., weights 218 of FIG. 2). The enhanced RGB image can be provided to one or more downstream systems, such as one or more displays 118 of system 100 for displaying in optional step 410, provided to one or more image processing systems for further image processing, provided to one or more storage systems, and/or used for any other purpose for which medical images are used.

Figure 6:
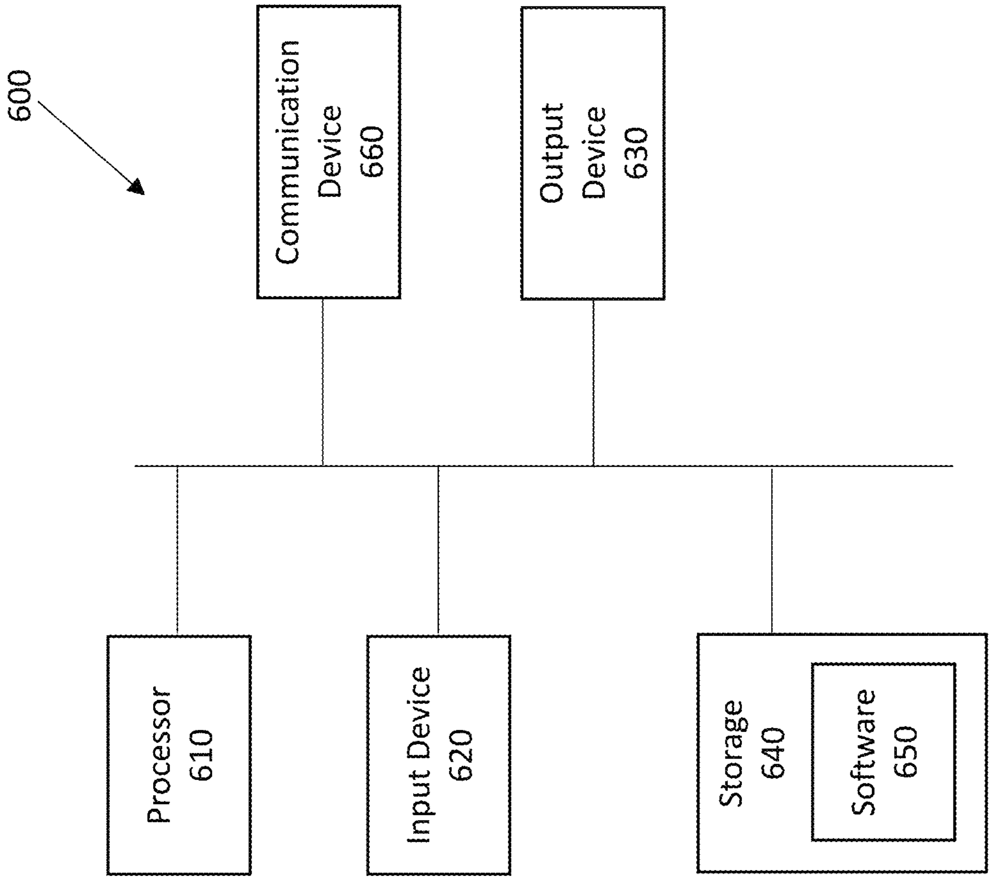
FIG. 6 illustrates an exemplary computing system.

FIG. 6 illustrates an example of a computing system 600, which can be used for one or more of components of system 100 of FIG. 1 and/or system 200 of FIG. 2, such as one or more of camera head 108, camera control unit 112, image processing unit 116, illuminator 120, and/or processor 206. System 600 can be a computer connected to a network, such as one or more networks of hospital, including a local area network within a room of a medical facility and a network linking different portions of the medical facility. System 600 can be a client or a server. As shown in FIG. 6, system 600 can be any suitable type of processor-based system, such as a personal computer, workstation, server, handheld computing device (portable electronic device) such as a phone or tablet, or dedicated device. The system 600 can include, for example, one or more of input device 620, output device 630, one or more processors 610, storage 640, and communication device 660. Input device 620 and output device 630 can generally correspond to those described above and can either be connectable or integrated with the computer.

Input device 620 can be any suitable device that provides input, such as a touch screen, keyboard or keypad, mouse, gesture recognition component of a virtual/augmented reality system, or voice-recognition device. Output device 630 can be or include any suitable device that provides output, such as a display, touch screen, haptics device, virtual/augmented reality display, or speaker.

Storage 640 can be any suitable device that provides storage, such as an electrical, magnetic, or optical memory including a RAM, cache, hard drive, removable storage disk, or other non-transitory computer readable medium. Communication device 660 can include any suitable device capable of transmitting and receiving signals over a network, such as a network interface chip or device. The components of the computing system 600 can be connected in any suitable manner, such as via a physical bus or wirelessly.

Processor(s) 610 can be any suitable processor or combination of processors, including any of, or any combination of, a central processing unit (CPU), graphics processing unit (GPU), field programmable gate array (FPGA), and application-specific integrated circuit (ASIC). Software 650, which can be stored in storage 640 and executed by one or more processors 610, can include, for example, the programming that embodies the functionality or portions of the functionality of the present disclosure (e.g., as embodied in the devices as described above). For example, software 650 can include one or more programs for execution by one or more processor(s) 610 for performing one or more of the steps of method 400.

Software 650 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 640, that can contain or store programming for use by or in connection with an instruction execution system, apparatus, or device.

Software 650 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport computer readable medium can include, but is not limited to, an electronic, magnetic, optical, electromagnetic, or infrared wired or wireless propagation medium.

System 600 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 600 can implement any operating system suitable for operating on the network. Software 650 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method of generating an RGB image of tissue comprising:
- receiving pixel values generated by at least one color filter array imaging sensor based on light received from a scene that comprises tissue, the pixel values comprising pixel values of a plurality of different colors;
- converting the pixel values to a luminance-chrominance color space, wherein luminance values in the luminance-chrominance color space are generated from pixel values of only one of the plurality of different colors;
- performing at least one image processing procedure in the luminance-chrominance color space; and
- generating an RGB image of the tissue by converting from the luminance-chrominance color space to an RGB color space.

2. The method of claim 1, wherein the pixel values comprise red, green, and blue pixel values.

3. The method of claim 2, wherein the luminance values are generated from only the green pixel values.

4. The method of claim 1, wherein at least some of the luminance values are equal to corresponding pixel values of the only one of the plurality of different colors.

5. The method of claim 4, wherein at least some of the luminance values are generated by spatially interpolating based on pixel values of the only one of the plurality of different colors.

6. The method of claim 1, wherein the light received from the scene comprises reflected light generated by different color illuminators of an illumination system.

7. The method of claim 6, wherein the chrominance values of the chrominance-luminance color space image are calculated from weights determined based on a response of the at least one color filter array imaging sensor to light generated by the different color illuminators of the illumination system.

8. The method of claim 6, wherein the at least one color filter array imaging sensor comprises red, green, and blue pixels and the different color illuminators comprise red, green, and blue illuminators.

9. The method of claim 1, wherein weights used for converting the pixel values to the luminance-chrominance color space are used to convert from the luminance-chrominance color space to the RGB color space for generating the RGB image of the tissue.

10. The method of claim 1, wherein the scene is an endoscopic scene.

11. The method of claim 1, wherein the at least one image processing procedure comprises at least one of sharpening, denoising, feature extraction, and image stabilization.

12. The method of claim 1, wherein converting the pixel values to a luminance-chrominance color space comprises demosaicing and leakage correction.

13. The method of claim 1, wherein the at least one color filter array imaging sensor comprises a Bayer sensor.

14. A system comprising one or more processors, memory, and one or more programs stored in the memory for execution by the one or more processors and including instructions for:

receiving pixel values generated by at least one color filter array imaging sensor based on light received from a scene that comprises tissue, the pixel values comprising pixel values of a plurality of different colors;

converting the pixel values to a luminance-chrominance color space, wherein luminance values in the luminance-chrominance color space are generated from pixel values of only one of the plurality of different colors;

performing at least one image processing procedure in the luminance-chrominance color space; and generating an RGB image of the tissue by converting from the luminance-chrominance color space to an RGB color space.

15. The system of claim 14, further comprising an imager that comprises the at least one color filter array imaging sensor.

16. The system of claim 15, wherein the imager comprises an endoscopic imager.

17. The system of claim 16, wherein the endoscopic imager is a chip-on-tip endoscope.

18. The system of claim 14, further comprising an illumination system for illuminating the scene.

19. The system of claim 14, wherein the pixel values comprise red, green, and blue pixel values.

20. The system of claim 19, wherein the luminance values are generated from only the green pixel values.

21. The system of claim 14, wherein at least some of the luminance values are equal to corresponding pixel values of the only one of the plurality of different colors.

22. The system of claim 21, wherein at least some of the luminance values are generated by spatially interpolating based on pixel values of the only one of the plurality of different colors.

23. The system of claim 14, wherein the light received from the scene comprises reflected light generated by different color illuminators of an illumination system.

24. The system of claim 23, wherein the chrominance values of the chrominance-luminance color space image are calculated from weights determined based on a response of the at least one color filter mosaic imaging sensor to light generated by the different color illuminators of the illumination system.

25. The system of claim 23, wherein the at least one color filter mosaic imaging sensor comprises red, green, and blue pixels and the different color illuminators comprise red, green, and blue illuminators.

26. The system of claim 14, wherein weights used for converting the pixel values to the luminance-chrominance color space are used to convert from the luminance-chrominance color space to the RGB color space for generating the RGB image of the tissue.

27. The system of claim 14, wherein the scene is an endoscopic scene.

28. The system of claim 14, wherein the at least one image processing procedure comprises at least one of sharpening, denoising, feature extraction, and image stabilization.

29. The system of claim 14, wherein converting the pixel values to a luminance-chrominance color space comprises demosaicing and leakage correction.

30. The system of claim 14, wherein the at least one color filter mosaic imaging sensor comprises a Bayer sensor.

31. A non-transitory computer readable storage medium storing one or more programs for execution by one or more processors of a computing system, the one or more programs comprising instructions that when executed by the one or more processors cause the computing system to perform a method comprising:

receiving pixel values generated by at least one color filter array imaging sensor based on light received from a scene that comprises tissue, the pixel values comprising pixel values of a plurality of different colors;

converting the pixel values to a luminance-chrominance color space, wherein luminance values in the luminance-chrominance color space are generated from pixel values of only one of the plurality of different colors;

performing at least one image processing procedure in the luminance-chrominance color space; and generating an RGB image of the tissue by converting from the luminance-chrominance color space to an RGB color space.

* * * * *